United States Patent [19]

Kufe

[11] Patent Number: 4,963,484

[45] Date of Patent: Oct. 16, 1990

[54] GENETICALLY ENGINEERED POLYPEPTIDES WITH DETERMINANTS OF THE HUMAN DF3 BREAST CARCINOMA-ASSOCIATED ANTIGEN

[75] Inventor: Donald W. Kufe, Wellesley, Mass.

[73] Assignee: Dana-Farber Cancer Institute, Inc., Mass.

[21] Appl. No.: 149,831

[22] Filed: Jan. 29, 1988

[51] Int. Cl.$^5$ .................. C12D 21/00; C12N 1/20; C12N 15/00; C07H 15/12

[52] U.S. Cl. .................. 435/69.3; 435/172.3; 435/252.3; 435/252.33; 435/320; 536/27; 935/1; 935/29; 935/72; 935/73

[58] Field of Search .............. 435/68, 252.3, 252.33, 435/172.3, 320; 536/27

[56] References Cited

PUBLICATIONS

Sekine et al., J. Immunol. 135(5):3610, 1985.
Young et al., Science 222:788, 1983.
Basak et al., Virology 128:77–91, 1983.
Old et al., *Principles of Gene Manipulation*, Blackwell Scientific Publications (Oxford), p. 292.
D. M. Swallow et al., Nature, vol. 327, 82–84 (1987).
S. J. Gendler et al., Proc. Natl. Acad. Sci., U.S.A., vol. 84, 6060–6064 (1987).
S. J. Gendler et al., Abstract A—11, Biennial Intl. Breast Cancer Res. Conf., Miami (Mar. 1–5, 1987).

*Primary Examiner*—Robin L. Teskin
*Assistant Examiner*—Beth A. Burrous
*Attorney, Agent, or Firm*—Allan H. Fried

[57] ABSTRACT

A carbohydrate-free polypeptide coded for by a human DNA sequence of 309 nucleotides is immunologically reactive with monoclonal antibody against the human DF3 breast carcinoma-associated antigen. The nucleotide sequence is also useful as a probe to reveal restriction fragment length polymorphisms in human DNA.

10 Claims, 4 Drawing Sheets

GENETICALLY ENGINEERED POLYPEPTIDES WITH DETERMINANTS OF THE HUMAN DF3 BREAST CARCINOMA-ASSOCIATED ANTIGEN

BACKGROUND AND OVERVIEW OF THE INVENTION

Women with breast carcinoma tend to have elevated serum levels of a molecular antigenic determinant referred to as the DF3 antigen (DF3). This provides the basis for a currently used diagnostic assay in which samples of a woman's serum are reacted with antibodies that bind specifically to DF3 (anti-DF3 antibodies; D. F. Hayes et al, J. Clin. Oncol. 4, 1542–1550; D. F. Hayes et al, J. Clin. Invest. 75, 1671–1678, 1985). The current invention relates to genetically engineered molecules that carry an immunologically active portion of the DF3 antigen; i.e., one that reacts with anti-DF3 antibodies. The molecules can be used to improve the reproducibility of the diagnostic assay. They can also be used as the basis for an alternative, more sensitive assay. In a related invention, individual women can be categorized as to their genetic material that determines the structure of DF3.

It has been demonstrated that naturally occurring DF3, that occurring in human breast carcinoma cells or the plasma of patients with breast cancer, is a member of a family of related but not identical high-molecular weight tumor-associated antigens (M. Abe et al, J. Immunol. 139, 257–261, 1987). Naturally occurring DF3 has been partially characterized as a high molecular weight mucin-like glycoprotein (H. Sekine et al., J. Immunol 135, 3610–3615, 1985; M. Abe et al., J. Cell Physiol. 126, 126–132, 1986), a molecule with both a polypeptide component and a carbohydrate component. The polypeptide component is comprised of one or more chains, each consisting of amino acids linked end-to-end in a specific sequence. On the average, it accounts for about 15 percent of the DF3 molecule, there being batch-to-batch variability and, within each batch, molecule-to-molecule variability, in the ratio of polypeptide to carbohydrate. As a result DF3 antigen is a collection of closely related but not necessarily identical molecules having the common property that they react with anti-DF3 antibodies. In human MCF-7 breast carcinoma cells, the antigen consists of two distinct glycoproteins with molecular weights in the range of 330 and 450 kilodaltons (kd), respectively (H. Sekine et al., J. Immunol 135, 3610–3615, 1985; M. Abe et al., J. Cell Physiol. 126, 126–132, 1986). DF3 antigen that circulates in the plasma of patients with breast cancer also has molecular weights ranging from approximately 300 to 450 kd (D. Hayes et al J. Clin. Invest. 75, 1671–1678, 1985).

In the currently used diagnostic assay for DF3, interpretation of the results requires that controls involving known amounts of DF3 be run. DF3 isolated from extracts of carcinoma cells is used to calibrate the assay. However, because of the above noted variability in the structure of DF3 antigen from molecule to molecule and from batch to batch, it would be advantageous to have a method of preparing a more reproducible version of the antigen. Improved reproducibility would be achieved if a carbohydrate-free polypeptide, capable of reacting with anti-DF3 antibody could be prepared. Previous work with the naturally occurring version had suggested that the carbohydrate portion of DF3 was essential for reaction with the anti-DF3 antibody. Nevertheless, in the current invention, synthesis of carbohydrate-free polypeptides with an antigenic determinant capable of reacting with anti-DF3 antibody (DF3 polypeptides), was achieved. Furthermore, these DF3 polypeptides can be synthesized in bacteria, which are expected to provide a less costly means of producing it.

The ability to synthesize an antigenically active polypeptide in bacteria also provides the basis for an alternative, potentially superior, means of detecting DF3 in human sera. In bacteria, the polypeptide can be synthesized with a higher specific radioactivity than is possible in human cells. It can then be used in a competition assay, one where anti-DF3 antibodies are allowed to react with a mixture of radioactive DF3 polypeptide that was synthesized in bacteria and nonradioactive antigen from the person's serum. This type of assay has been used with the carcinoembryonic antigen (CEA; See, for example, Feb. 1983 package insert for Carcinoembryonic Antigen Radioimmunoassay, Roche Diagnostics, Nutley, N.J. 07110) The nonradioactive antigen will compete with the radioactive DF3 for antibody binding sites, the diminished binding of radioactivity being an index of the amount of DF3 antigen in the person's serum. This type of assay is expected to be able to detect smaller amounts of antigen in a person's serum than the currently used assay can.

In an example of the invention, a DF3 polypeptide was synthesized in the prokaryotic organism, Escherichia coli (E. coli), a bacterium. Although there is still uncertainty as to both the number of polypeptide chains in a naturally occurring DF3 antigen molecule and the size of each chain, it is likely that the synthetic DF3 polypeptide represented less than a complete naturally occurring chain. Incomplete synthesis of an antigen polypeptide chain is a possible result of the procedure used to initially isolate DNA coding for an antigenically active site. First, messenger RNA (mRNA) was isolated from human breast carcinoma cells, which are known to synthesize the antigen. DNA copies of the mRNA were then made. (Failure to isolate intact mRNA molecules or synthesize complete DNA copies are two possible reasons why incomplete synthesis of an antigen chain is ultimately achieved.) Each DNA fragment was then attached to the DNA of a bacterial virus such that, if the fragment contained the ability to direct the synthesis of human DF3 polypeptide, that peptide would be expressed as part of a fused polypeptide also containing the bacterial polypeptide, beta galactosidase. The resulting population of DNA molecules was distributed among a very large number of bacterial cells by a transfection process. At a subsequent step, each bacterial cell was tested for the ability to direct the synthesis of a polypeptide that would react with anti-DF3 antibody. Prior to completing the test, there was uncertainty as to whether the procedure employed would be successful in generating bacteria capable of making an antigenically active polypeptide: Not only would the polypeptide lack the carbohydrate portion it has in humans, there was an excellent chance that it would be smaller than its intact human form. As it turned out, several bacteria that produced antigenically active polypeptide were found, the one presented in detail here being typical of the group.

Regardless of the precise relationship of the E. coli produces DF3 polypeptide to the naturally occurring one, the results presented above provide the following picture:

(1) the polypeptide component of DF3 has antigenic activity in the absence of any carbohydrate component;

(2) probably only a portion of the polypeptide (not more than 103 amino acids) is required for antigenic activity; and (3) the antigenically active portion of the DF3 polypeptide retains its antigenic activity even when part of a polypeptide that is partly comprised of polypeptide sequences naturally foreign to it. As to this latter point, consider the fact that, in E. coli, the DF3 polypeptide was joined to the 116,000 dalton bacterial polypeptide, beta galactosidase. An advantage of this latter property is that the antigenically active site can be made part of a tyrosine-rich polypeptide, and radioactive iodine can be attached to the tyrosine residues, thereby increasing the specific radioactivity of the antigenic probe for use in the competition diagnostic assay.

Electrophoretic mobility patterns of an antigen are a reflection of its structure. The electrophoretic mobility patterns for circulating DF3 antigen are heterogeneous and differ among individuals (D. Hayes et al J. Clin. Invest. 75, 1671–1678, 1985). Subsequent studies in family members have demonstrated that the electrophoretic mobility pattern of plasma DF3 antigen is genetically determined by codominant expression of multiple alleles at a single locus (D. Hayes et al, Blood, 1988, in press).

The aforementioned electrophoretic and genetic studies would not, however, make it obvious how one could detect the changes in DNA structure responsible for the person-to-person variations in DF3 structure. Person-to-person variation in DNA structure of specific genes had been successfully demonstrated for some other genes using the technique of restriction fragment length polymorphism (RFLP). In RFLP analysis, one analyzes the size of DNA fragments that carry a particular gene after controlled digestion (by a restriction endonuclease) of that person's DNA. The technique can be used to categorize individuals genetically and also assist in identifying the individual who is the source of a particular tissue or group of body cells. Applicant used RFLP analysis to investigate the size of DNA fragments that carry the gene for the 103-amino acid antigenically active DF3 polypeptide. He discovered that indeed such RFLP analysis reveals variations in DNA structure that correlated with the variations in size of the circulating antigens. Whether there is a correlation between a particular DNA structure and a predisposition to breast cancer is unknown.

Of interest is a report which describes the isolation of a partial cDNA clone (pMUC10) which codes in part for urinary mucins (PUMs) (D. Swallow et al, Nature 328, 82–84, 1987). The report is of interest because the clone codes for CA1, an antigenic determinant also found on naturally occurring DF3 antigen. Furthermore, an RFLP analysis of human DNA using the pMUC10 probe disclosed EcoRI restriction fragments similar in size to those found in the present study (S. Gendler et al, Proc. Natl. Acad. Sci. U.S. 84: 6060–6064, 1987). Nevertheless it is uncertain to what extent, if any, pMUC10 codes for sequences within the 103-amino acid and 600-amino acid DF3 polypeptides of the present invention. In the first place, Ca1 reacts with a wide range of human tumors (F. Ashall et al, Lancet 2, 1–6, 1982; J. McGee et al, Lancet 2, 7–10, 1982). Additionally, the binding site on the DF3 glycoprotein for anti-Ca1 antibodies is distinct from that for anti-DF3 antibodies (M. Abe et al, J. Immunol. 139: 257–261, 1987).

Indeed, none of the aforementioned reports on pMUC10 disclosed that it codes for a determinant recognized by anti-DF3 antibody.

SUMMARY OF THE INVENTION

In one aspect, the invention is a polypeptide that:

(1) is free or substantially free of bound carbohydrate; and (2) includes all or a portion of the amino acid sequence that is coded for by the human nucleotide sequence of

| CGCACGGCTG | GGGGGGCGGT | |
|---|---|---|
| .CGTG..... | C...C..... | |
| .......... | .......... | |
| .......... | G...G..... | |
| .......... | .......... | |
| | | |
| GGAGCCCGGG | GCCGGCCTGC | |
| .......... | .......... | |
| .......... | .......... | |
| .......... | .......... | |
| .......... | .......... | |
| | | |
| TCTCCGGGGC | CGAGGTGACA | 60 |
| .......... | .......... | 120 |
| .G........ | .......... | 180 |
| .......... | .......... | 240 |
| .......... | .......... | 300 | a dot indicating that the nucleotide is identical to the one directly above it in the mode of representation used here.

In another aspect, the invention is an antigen that reacts with anti-DF3 antibody and whose polypeptide component was synthesized in a non-human cell under the direction of a human nucleotide sequence.

In another aspect, the invention is a recombinant DNA molecule that codes for a polypeptide capable of reacting with an anti-DF3 antibody; in another aspect, the invention is a prokaryotic organism containing such a recombinant DNA molecule in a form in which it can be expressed to direct the synthesis of a polypeptide that reacts with an anti-DF3 antibody. [A recombinant DNA molecule, in the present application, is one which does not occur in nature until human intervention leads to its construction and which, except for a specific desired nucleotide sequence, is free or substantially free of human DNA.]

In another aspect, the invention is a DNA molecule containing the sequence of 309 nucleotides depicted above, said DNA molecule being substantially free of other mammalian DNA.

In another aspect, the invention is a process of hybridizing a DNA molecule comprising the sequence of 309 nucleotides depicted above against restriction enzyme generated fragments of human DNA that have been fractionated on the basis of size.

In another aspect, the enzyme is a process which comprises binding an anti-DF3 antibody to a polypeptide which was synthesized in a non-human cell under the direction of a human nucleotide sequence.

In subgeneric aspects of the above inventions that involve DF3 polypeptides, the entire polypeptide sequence coded for by the human DNA component of pDF3.9 are required and, in other subgeneric aspects, those are the only naturally occurring DF3 sequences present.

In additional subgeneric aspects of the above inventions that involve anti-DF3 antibodies, the anti-DF3 antibody of the invention is that produced by hybridoma No. DF3 of the laboratory of Donald W. Kufe, Dana-Farber Cancer Institute, Boston, Mass. (Hybridoma No. DF3).

BRIEF DESCRIPTION OF THE DRAWINGS

FIG. 1: Immunological identification of pDF9.3 encoded recombinant antigen. Lambda gt11 and pDF9.3 recombinant phage were used to lysogenize E. coli Y1089. Protein extracts were prepared from the lysogens and 10 ul of the bacterial lysates were electrophoresed in SDS/7.5% polyacrylamide gels, electroblotted onto nitrocellulose and, after the nitrocellulose was blocked with 1% BSA in Tris-buffered saline plus Tween 20, it was incubated with anti-beta-galactosidase antibody (Lane 1) or MAb DF3 (Lane 2). MAb DF3 was also preincubated with 10 ng (Lane 3), 100 ng (Lane 4) and 500 ng (Lane 5) of purified DF3 antigen prior to probing the filters. Antibody binding was detected by an enzyme linked immunoabsorbant assay (the antibody was reacted with goat anti-mouse IgG linked to alkaline phosphatase) using nitroblue tetrazolium as substrate and developed with 5-bromo-4-chloro-3-nitryl phosphate (Reagents were those of the Protoblot Lambda gt11 Immunoscreening System, Promega Biotec, Madison, Wis.). Several apparent proteolytic breakdown products are noted using the anti-beta-galactosidase antibody.

FIG. 2: Southern blot analysis of genomic DNA with the pDF9.3 probe. DNAs (20 ug) from human tumor cell lines were digested to completion with EcoRI (A), PstI (B) and HindIII (C), and electrophoresed in 0.6% agarose gels. The gels were denatured and the DNA fragments transferred to nylon filters. The filters were hybridized with the $^{32}$P-labeled pDF9.3 cDNA insert. The filters were then washed and exposed to x-ray film.

FIG. 3: Northern blot analysis with pDF9.3 and immunoblotting with MAb DF3. A. Total cellular RNA (20 ug) from human tumor cell lines was electrophoresed in a 1% agarose/formaldehyde gel, transferred to nitrocellulose and hybridized with the $^{32}$P-labeled pDF9.3 cDNA insert. B. Extracts of the human tumor cells were analyzed by SDS/3-15% polyacrylamide gel electrophoresis, immunoblotted with MAb DF3, and then reacted with rabbit anti-mouse Ig and $^{125}$I-labeled protein A.

DETAILED DESCRIPTION

Library screening. An oligo (dT) primed cDNA library was prepared from human MCF-7 breast carcinoma cells in lambda gt11 (P. Walter et al. *Proc. Natl. Acad. Sci., U.S.A.* 82, 7889-7893, 1985). Immunologic screening of the lambda gt11 library was performed as previously described (R. A. Young et al., *Proc. Natl. Acad. Sci., U.S.A.* 80: 1194-1198, 1983) using affinity purified MAb DF3 (0.25 ug/ml) [D. Kufe et al, *Hybridoma* 3, 223-232, 1984, describes the isolation of the hybridoma, presently referred to as Hybridoma No. DF3 in the laboratory of Donald W. Kufe, Dana-Farber Cancer Institute, Boston, Mass. The hybridoma was injected into mice, the ascites recovered, and the Mab DF3 antibodies purified by the MAPS II kit of Biorad, Richmond, Calif.] and anti-mouse IgG conjugated with alkaline phosphatase (Promega Biotech, Madison, Wis.). Positive plaques were isolated and the phage was further purified to homogeneity by repeated antibody screening. DNA was isolated from MAb DF3 positive recombinant phage, digested with EcoRI and electrophoresed in 1.2% agarose gels containing ethidium bromide to determine the size of the insert.

Analysis of lysogens for fusion protein. Lysogenization of E. coli Y1089 with phage and induction of fusion protein with isopropyl-beta-D-thiogalactoside (IPTG) were performed as described previously (R. A. Young et al., *Proc. Natl. Acad. Sci., U.S.A.* 80: 1194-1198, 1983, R. A. Young et al, *Science* 222: 778-782, 1983). The lysate of IPTG induced lysogen was subjected to electrophoresis in SDS/7.5% polyacrylamide gels (U. K. Laemmli, *Nature* 227, 680-685, 1970) and transferred to nitrocellulose filters for immunoscreening (W. N. Burnette, *Anal. Biochem.* 112: 195-203).

Southern and Northern blot analyses. The human breast carcinoma cell lines (BT-20, T47D, MCF-7, ZR-75-1), an ovarian carcinoma cell line (OV-D) and the HL-60 promyelocytic leukemia cell line were maintained in exponential phase (H. Abe et al, *J. Immunol.* 139: 257-261, 1987; E. Friedman et al., *Cancer Res.* 46, 5189-5194, 1986; E. Sariban et al, *Nature* 316, 64-66, 1985). BT-20 is ATCC No. HTB 19, T47D is ATCC NO. HTB 133, MCF-7 is ATCC No. HTB 22, ZR-75-1 is ATCC No. ATC CRL 1500, and HL-60 is ATCC No. ATC CCL 240 at the American Type Culture Collection, Rockville, Md. High molecular weight DNA and total cellular RNA were isolated by the guanidine isothiocyanate/cesium chloride method (L. G. Davis et al, *Basic Methods in Molecular Biology*, Elsevier, N.Y. p. 130-135, 1986). The DNA was digested with EcoRI, PstI or HindIII. The DNA fragments were separated by electrophoresis in 0.6% agarose gels and then transferred to nylon membranes. The prehybridization and hybridization conditions were as described in the Zeta Probe manual (Bio-Rad Laboratories, Richmond, Calif.). The purified RNA (20 ug) was analyzed by electrophoresis in 1% agarose-formaldehyde gels followed by transfer to nitrocellulose paper. The hybridization conditions were as described previously (E. Sariban et al, *Nature* 316, 64-66, 1985). The pDF9.3 cDNA probe was labeled with [$^{32}$P] dCTP (Amersham, Arlington Heights, Ill.) by the random primer method (A. P. Beinburg et al, *Anal. Biochem.* 132, 6-13, 1984) to a specific activity of approximately $10^9$ cpm/ug DNA.

Immunoblot analysis. Cells were suspended in phosphate buffered saline (PBS) (pH 7.4), 0.2 mM phenylmethylsulfonyl fluoride and aprotinin (0.015 trypsin inhibitor units/ml). The suspensions were sonicated and protein concentration was determined by the Bio-Rad protein assay (Bio-Rad Laboratories). The protein samples (100 ug) were analyzed by electrophoresis in SDS/3-15% gradient polyacrylamide gels and transferred to nitrocellulose paper (H. Towbin et al, *Proc. Natl. Acad. Sci. U.S.A.* 76: 4350-4354, 1979). The nitrocellulose filters were washed with 5e bovine serum albumin in PBS for 1 h at room temperature (25° C.), incubated with MAb DF3 (0.25 ug/ml) for 2 h, rabbit anti-mouse Ig for 1 h and then $^{125}$I-labeled protein A for 2 h. The filters were washed five times, dried and exposed to x-ray film.

Nucleotide sequence analysis. The 309 bp pDF9.3 cDNA insert was subcloned into the EcoRI site of E. coli phage M13mp8 and M13mp9. The DNA sequence was determined by sequencing both strands via the dideoxy chain termination method (F. Sanger et al., Proc. Natl. Acad. Sci. U.S.A. 74, 5463–5467, 1987) using Klenow fragment DNA polymerase I (New England Biolabs, Beverly, Mass.) and [alpha-$^{35}$S]dCTP (Amersham).

EXAMPLES

Figure 1:
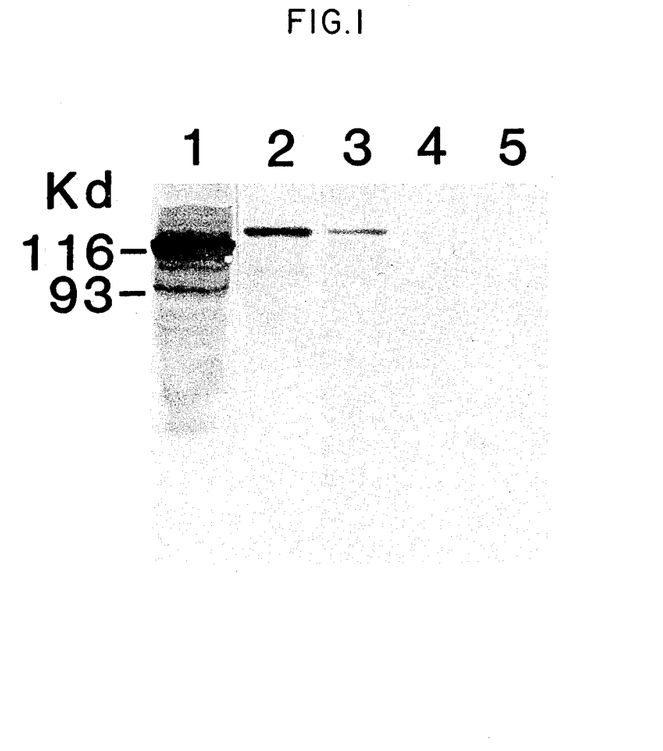

Isolation and characterization of cDNA clones coding for DF3 antigen. MAb DF3 was used to screen the lambda gt11 library prepared from MCF-7 cells. Screening of 800,000 plaques yielded three positive clones which were further purified by repeated antibody screenings. Physical mapping showed that each of these recombinant clones contained inserts of similar size and that they had similar restriction maps (data not shown). One clone, designated pDF9.3 was characterized further. A beta-galactosidase fusion protein was prepared by infecting E. coli Y1089 with pDF9.3 and then analyzed by immunoblotting. The lambda gt11 lysogen produced a protein corresponding in molecular weight and antigenicity to beta-galactosidase (FIG. 1, Lane 1). MAB DF3 was unreactive with beta-galactosidase and other antigens present in the bacterial lysate (data not shown). In contrast, the recombinant pDF9.3 lysogen produced a fusion protein with an estimated mass of 126 kd which reacted with both MAb DF3 (FIG. 1, Lane 2) and the anti-beta-galactosidase antibody (data not shown).

Competition assays were also performed to further confirm that the epitope expressed by pDF9.3 shares homology with that identified by MAb DF3 on the DF3 glycoprotein. Thus, MAb DF3 was preincubated with purified DF3 antigen (H. Abe et al, *J. Immunol.* 139: 257–261, 1987) before immunoblot analysis of the pDF9.3 fusion protein. Preincubation of MAb DF3 with increasing amounts of purified DF3 antigen progressively inhibited reactivity of the antibody with the fusion protein (FIG. 1, Lanes 3–5). This finding indicates that the epitope on the fusion protein originates from the same reading frame that codes for the DF3 epitope.

Figure 2A:
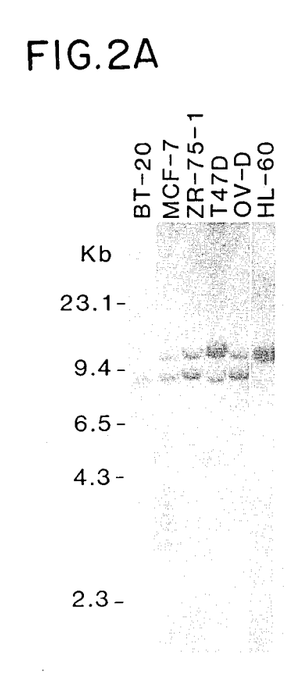
Figure 2B:
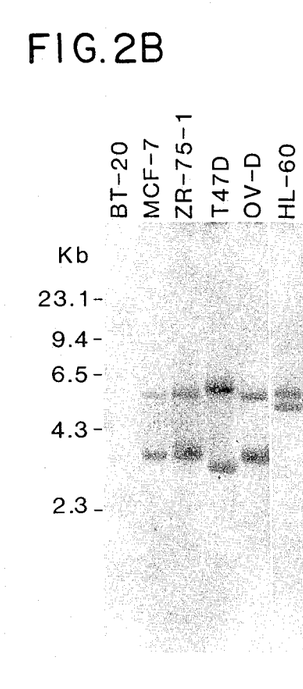
Figure 2C:
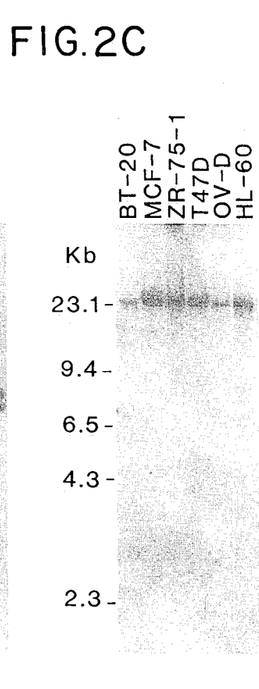

Southern blot analysis of genomic DNA. Identification of the cDNA was further studied by Southern blot hybridizations using $^{32}$P-labeled pDF9.3 prepared by subcloning the 309 bp insert into the EcoRI site of pUC8. Southern blot analyses of genomic DNAs from the human tumor cell lines digested with EcoRI, PstI, and HindIII are shown in FIG. 2. Hybridization of the 309 bp cDNA with the EcoRI and PstI DNA digests revealed restriction fragment length polymorphisms. The EcoRI digest yielded two fragments ranging from 7 to 12 kb in size for DNAs from each of the cell lines except BT-20. [In FIG. 2b, for BT-20, a faint band migrated the same distance as the approximately 3.0 kb band from MCF-7 cells.] Similar findings were obtained with the PstI fragments which ranged in size from 3.5 to 6 kb. The single EcoRI and PstI restriction fragments obtained with BT-20 DNA indicates the presence of two alleles of identical size or only a single allele. In contrast to these results, digestion of each of the DNA preparations with HindIII revealed only a single fragment of 23 kb. This finding would correspond to the absence of a HindIII restriction site in the alleles identified by pDF9.3.

Figure 3A:
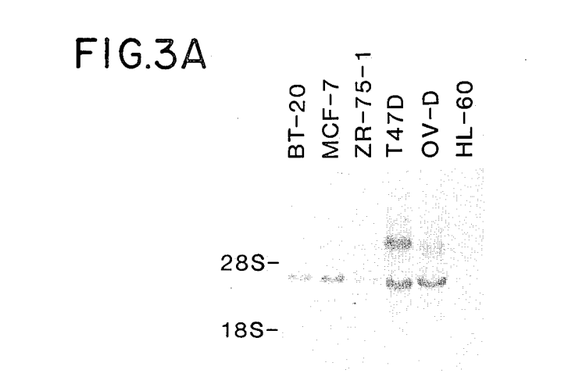

Northern and Western blot analyses of DF3 expression. Total cellular RNA was prepared from each of the human tumor cell lines and monitored by Northern analysis for transcripts which hybridized to the pDF9.3 probe. A single 4.7 kb mRNA was detectable in BT-20 cells (FIG. 3A). In contrast, cell lines derived from the other breast and ovarian carcinomas expressed two transcripts which ranged in size from approximately 4.1 to 7.1 kb (FIG. 3A). Furthermore, no hybridization was detectable with RNA from HL-60 cells (FIG. 3A).

Figure 3B:
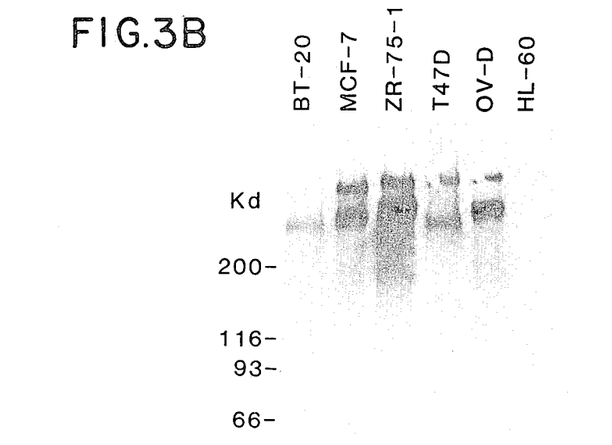

These findings by Northern blot analysis were compared to those obtained by immunoblotting with MAb DF3 and extracts prepared from each of the cell lines. The results indicated concordance in patterns of expression at the RNA and protein levels (FIG. 3B). Thus, BT-20 cells expressed a single transcript and a single DF3 glycoprotein, while the other epithelial cell lines expressed two transcripts and two DF3 antigens. Moreover, HL-60 cells had no detectable RNA and no detectable MAb DF3 reactive species. These findings further suggested that the transcripts detected by Northern analysis code for the DF3 core protein and that the size of these transcripts determines the size of the MAb DF3 reactive glycoproteins.

Figure 4:
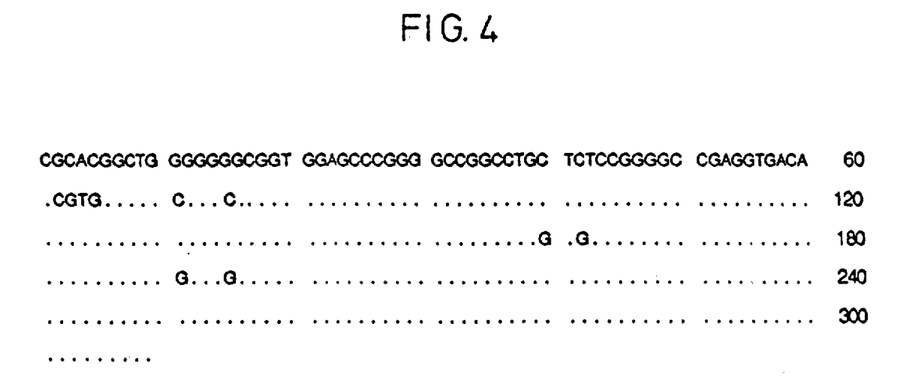
FIG. 4: Nucleotide sequence of the pDF9.3 cDNA insert.

Nucleotide sequence of pDF9.3. The reactivity of the fusion protein with MAb DF3 indicated that the cDNA insert contained an open reading frame which encodes for the DF3 epitope. The nucleotide sequence of pDF9.3 was found to be highly rich (85%) in GC base pairs (FIG. 4). Moreover, the sequence was found to consist entirely of 60 bp tandem repeats. These repeats were nearly identical with the exception of some transversions (FIG. 4). Furthermore, comparison of the pDF9.3 sequences with that of all genes with known sequences failed to reveal any significant homology.

Other systems for the invention

Prokaryotic organisms, especially bacteria, are preferred organisms for expressing the DF3 polypeptide. Many bacterial expression systems are well documented.

Techniques for taking a DNA sequence of known nucleotide sequence, such as pDF9.3, and inserting it into a plasmid or other DNA molecule so that its expression can be achieved, and preferably regulated, are well established.

Techniques for allowing an antibody to react with an antigen are well documented.

Expression of an amino acid sequence from pDF9.3

Insertion of pDF9.3 into a plasmid can result in the expression of any one of six amino acid sequences, depending on which of its two DNA strands is in the same strand as the controlling plasmid promoter and depending upon which one of the three possible reading frames for pDF9.3 is in phase with the initiation codon for the polypeptide that is fused to the pdf9.3-coded polypeptide. [Note that in FIG. 4, translation of the depicted strand will proceed from left to right.]

DISCUSSION

It has previously been demonstrated that DF3 antigen in human breast tumors and milk is comprised of mucin-like glycoproteins with molecular weights ranging from 300 to over 450 kd (H. Sekine et al., *J. Immunol* 135, 3610–3615, 1985; M. Abe et al., *J. Cell Physiol.* 126, 126–132, 1986). DF3 antigenicity was found to be sensitive to both neuraminidase and proteases (H. Sekine et al., *J. Immunol* 135, 3610–3615, 1985; M. Abe et al., *J. Cell Physiol.* 126, 126–132, 1986). These results suggested that sialyl oligosaccharides on a peptide backbone are required for DF3 antigenicity. In the present study, MAb DF3 positive plaques were isolated using a lambda gt11 cDNA library prepared from human MCF-7 breast carcinoma cells. The MCF-7 cells have been previously shown to express DF3 antigen (H. Abe et al, *J. Immunol.* 139: 257–261, 1987). One of the positive lambda clones (pDF9.3) was further purified and found to produce a beta-galactosidase fusion protein which specifically reacted with MAb DF3. The reactivity of MAb DF3 with plaques from this expression library and the fusion protein indicates that this antibody reacts with the core protein of DF3 antigen. However, DF3 antigenicity has also been shown to be sensitive to neuraminidase (H. Sekine et al., *J. Immunol* 135, 3510–3615, 1985; M. Abe et al., *J. Cell Physiol.* 126, 126–132, 1986). Thus, MAb DF3 binding to the protein may be enhanced by the presence of glycosidic linkages.

Although patients with breast cancer and certain other carcinomas have higher levels of circulating DF3 antigen, the electrophoretic mobilities of the MAb DF3 reactive species are similar to those in normal subjects (D. Hayes et al, *J. Clin. Invest.* 75, 1671–1678, 1985; H. Sekine et al, *J. Clin. Oncol.* 3: 1355–1363, 1985). Indeed, more recent results have indicated that the variation in electrophoretic mobility of circulating DF3 antigen among family members is related to a genetically determined polymorphism (D. Hayes et al; *Blood*, 1987, in press). The present findings support this genetic polymorphism. Thus, considerable fragment size variation was observed after hybridization of the pDF9.3 probe to EcoRI and PstI restriction digests of DNA from different cell lines. The EcoRI restriction fragments varied from 7 to 12 kb in size and the different cells had only one or two bands. Furthermore, the PstI fragments varied from 3.5 to 6 kb and each DNA preparation similarly yielded one or two bands. In contrast, hybridization of pDF9.3 probe to HindIII DNA digests revealed only one 23 kb band and indicated that this restriction enzyme has digestion sites outside the region identified by this probe.

The variation in allele size identified with pDF9.3 correlated with the presence of different sized transcripts. Thus, cells with two restriction fragments in the EcoRI or PstI DNA digests had two different sized mRNAs. In contrast, BT-20 cells had only one detectable restriction fragment in these DNA digests and expressed only one transcript. This relationship also extended to the variation in electrophoretic mobilities of DF3 antigen. BT-20 cells expressed a single MAb DF3 reactive species, while the other epithelial tumor cells expressed two DF3 antigens. Moreover, HL-60 cells had no detectable transcripts and no detectable DF3 antigen. Taken together, these findings support our previous findings that the heterogeneity of DF3 antigen production is controlled by multiple alleles at a single locus expressed in an autosomal codominant fashion (D. Hayes et al; *Blood*, 1987, in press).

The nucleotide sequence analysis of pDF9.3 provides a possible explanation for the variability in restriction fragment size and the polymorphic patterns of DF3 expression. In this regard, we have identified a 309 bp cDNA clone which consists of multiple tandem repeats. These repeats are GC rich and encompass 60 bp. Variation in the size of the DF3 alleles could thus be due to differences in the number of these repeats and occur as a result of unequal crossing-over events. The presence of closely related repeats may also explain the finding that MAb DF3 binds to two or more epitopes in the same DF3 molecule (D. Hayes et al, *J. Clin. Invest.* 75, 1671–1678, 1985). The total number of these repeats in the full length cDNA, however, requires further investigation.

Similar variable tandem repeats have been reported for other genes including those coding for carcinoembryonic antigen (W. Zimmerman et al, *Proc. Natl. Acad. Sci. U.S.A.* 84, 2960–2964, 1987), insulin (Q. I. Bell et al, *Nature* 295: 31–35, 1982), alpha- and beta-globulin (D. R. Higgs et al, *Nucleic Acid Res.* 9, 4213–4224, 1981; R. A. Spritz, *Nucleic Acid Res.* 9, 5037–5047, 1981), Epstein Barr virus (S. H. Speck et al, *Proc. Natl. Acad. Sci. U.S.A.* 83, 9298–9310, 1986), cHa-ras (D. J. Capon et al, *Nature* 302, 33–37, 1983), and a hypervariable minisatellite family (A. J. Jeffries et al, *Nature* 314: 67–73, 1985). Furthermore, the human complement receptor (CR1) gene consists of homologous repeats approximately 1.6 kb in size (V. M. Holers et al, *Proc. Natl. Acad. Sci. U.S.A.* 84, 2459–2463, 1987). Allelic variants of CR1 differ by 1.6 kb and also correlate with variations in size of both the CR1 transcripts and products (V. M. Holers et al, *Proc. Natl. Acad. Sci. U.S.A.* 84, 2459–2463, 1987). The lengths of most internal repeats, however, range between 120 and 300 bp (W. L. Li in *Evolution of Genes and Proteins*, Eds. M. Nei et al; Sinaur, Sunderland, Mass., p. 14–37, 1983). Moreover, homology of the internal repeats for many vertebrate proteins ranges between only 20 and 50% (W. L. Li in *Evolution of Genes and Proteins*. Eds. M. Nei et al, Sinaur, Sunderland, Mass., p. 14–37, 1983). In contrast, the internal repeats identified in the present study exhibit a particularly high degree of homology. This finding could suggest that the DF3 gene evolved more recently by duplication of a primordial gene or by exon shuffling.

What is claimed is:

1. A biologically pure double stranded DNA molecule containing in one strand a first nucleotide sequence that is all or a portion of the sequence

```
CGCACGGCTG  GGGGGGCGGT
.CGTG.....  C...C.....
..........  ..........
..........  G...G.....
..........  ..........
..........  ..........

GGAGCCCGGG            GCCGGCCTGC
..........            ..........
..........            .........G
..........            ..........
..........            ..........

TCTCCGGGGC  CGAGGTGACA   60
            ..........  ..........  120
            .G........  ..........  180
            ..........  ..........  240
            ..........  ..........  300
```

(a dot indicating that the nucleotide is identical to the one directly above it in the mode of representation used in this claim) and containing in the other strand a second nucleotide sequence complementary to the first nucleotide sequence said DNA molecule being substantially free of other mammalian DNA said portion coding for a polypeptide capable of reacting with an anti-DF3 antibody.

2. A prokaryotic organism containing a DNA molecule of claim 1 said DNA molecule being one which can be expressed to direct the synthesis of the polypeptide that reacts with an anti-DF3 antibody.

3. A double stranded DNA molecule of claim 1, that contains all of the sequence of 309 nucleotides set forth in that claim.

4. The purified double stranded DNA molecule of claim 3 that has been purified so that it is not in either a prokaryotic or eukaryotic organism.

5. A solution in which is dissolved the separated strands of a DNA molecule of claim 1.

6. The process of making a polypeptide which process comprises the steps of
   (1) introducing into a non-human cell a double stranded DNA molecule containing in one strand a first nucleotide sequence that is all or a portion of the sequence

```
CGCACGGCTG  GGGGGGCGGT
.CGTG.....  C...C.....
..........  ..........
..........  G...G.....
..........  ..........
..........

GGAGCCCGGG        GCCGGCCTGC
      ..........        ..........
      ..........        ..........
      ..........        ..........
      ..........        ..........

TCTCCGGGGC  CGAGGTGACA   60
```

-continued

```
..........  ..........   120
.G........  ..........   180
..........  ..........   240
..........  ..........   300
```

(a dot indicating that the nucleotide is identical to the one directly above it in the mode of representation used in this claim) and containing in the other strand a second nucleotide sequence complementary to the first nucleotide sequence such that the DNA molecule can be expressed to direct the synthesis of a polypeptide coded for by said nucleotide sequences and such that said portion codes for a polypeptide capable of reacting with an anti-DF3 antibody; and
   (2) culturing the non-human cell under conditions where the polypeptide coded for by the nucleotide sequences is synthesized.

7. The process of claim 6 in which all of the nucleotide sequence of claim 6 is introduced into the non-human cell.

8. The process of claim 6 in which a portion of the nucleotide sequence of claim 6 is introduced into the non-human cell.

9. The process of claim 7 in which the non-human cell is a prokaryotic cell.

10. The process of claim 8 in which the non-human cell is a prokaryotic cell.

* * * * *

UNITED STATES PATENT AND TRADEMARK OFFICE
CERTIFICATE OF CORRECTION

PATENT NO. : 4,963,484

DATED : Oct. 16, 1990

INVENTOR(S) : Donald W. Kufe

It is certified that error appears in the above—identified patent and that said Letters Patent is hereby corrected as shown below:

Column 4, line 22, delete the dot positioned at the right end of line 22 and insert the letter "G" in its place;

Column 6, line 58, "5e" should be "5%";
Column 8, line 31, the entire line should be underlined;
Column 8, line 43, the entire line should be underlined;
Column 11, line 1, delete the comma;

Column 11, line 26, delete the dot positioned at the right end of line 26 and insert the letter "G" in its place.

UNITED STATES PATENT AND TRADEMARK OFFICE
CERTIFICATE OF CORRECTION

PATENT NO. : 4,963,484            Page 2 of 2

DATED : Oct. 16, 1990

INVENTOR(S) : Donald W. Kufe

It is certified that error appears in the above-identified patent and that said Letters Patent is hereby corrected as shown below:

The sheet of drawing consisting of Fig. 4, should be added as shown on the attached page.

FIG. 4

| | | | | | |
|---|---|---|---|---|---|
| CGCACGGCTG | GGGGGGCGGT | GGAGCCCGGG | GCCGGCCTGC | TCTCCGGGGC | CGAGGTGACA | 60 |
| .CGTG..... | C...C..... | .......... | .......... | .......... | .......... | 120 |
| .......... | .......... | .......... | ........G | .G........ | .......... | 180 |
| .......... | G...G..... | .......... | .......... | .......... | .......... | 240 |
| .......... | .......... | .......... | .......... | .......... | .......... | 300 |
| .......... | | | | | |

Signed and Sealed this

Twelfth Day of May, 1992

*Attest:*

DOUGLAS B. COMER

*Attesting Officer*      *Acting Commissioner of Patents and Trademarks*

UNITED STATES PATENT AND TRADEMARK OFFICE
CERTIFICATE OF CORRECTION

PATENT NO. : 4,963,484

DATED : October 16, 1990

INVENTOR(S) : Donald W. Kufe

It is certified that error appears in the above-indentified patent and that said Letters Patent is hereby corrected as shown below:

In Column 1, between the Title and Background and Overview of the Invention, insert the following:

--Statement of Government Interest

Funding for the present invention was provided in part by the Government of the United States of America by virtue of Grant Nos. CA20531 and CA38879 by the National Institutes of Health. Thus, the Goverment of the United States has certain rights in and to the invention claimed herein. --

Signed and Sealed this

Twentieth Day of May, 1997

Attest:

BRUCE LEHMAN

Attesting Officer

Commissioner of Patents and Trademarks